United States Patent
Lee (10) Patent No.: US 9,857,319 B2
(45) Date of Patent: Jan. 2, 2018

(54) METHOD OF MEASURING DEPTH OF DAMAGE OF WAFER

(71) Applicant: LG SILTRON INCORPORATED, Gumi-si, Gyeongsangbuk-do (KR)

(72) Inventor: Kyu Hyung Lee, Gumi-si (KR)

(73) Assignee: LG SILTRON INCORPORATED, Seoul (KR)

( * ) Notice: Subject to any disclaimer, the term of this patent is extended or adjusted under 35 U.S.C. 154(b) by 172 days.

(21) Appl. No.: 15/025,880

(22) PCT Filed: Aug. 12, 2014

(86) PCT No.: PCT/KR2014/007480
§ 371 (c)(1),
(2) Date: Mar. 29, 2016

(87) PCT Pub. No.: WO2015/046752
PCT Pub. Date: Apr. 2, 2015

(65) Prior Publication Data
US 2016/0238544 A1  Aug. 18, 2016

(30) Foreign Application Priority Data

Sep. 30, 2013 (KR) .......................... 10-2013-0116346

(51) Int. Cl.
*G01N 23/207* (2006.01)
*H01L 21/66* (2006.01)

(52) U.S. Cl.
CPC ........... *G01N 23/207* (2013.01); *H01L 22/12* (2013.01); *G01N 2223/607* (2013.01); *G01N 2223/6116* (2013.01)

(58) Field of Classification Search
CPC ........... G01N 2223/607; G01N 23/207; G01N 23/20; G01N 23/18; G01N 2223/6462

(Continued)

(56) References Cited

U.S. PATENT DOCUMENTS

| 5,387,459 | A | 2/1995 | Hung |
| 9,678,023 | B2 * | 6/2017 | Kim ..................... G01N 23/207 |
| 2008/0271667 | A1 | 11/2008 | Ishibashi et al. |

FOREIGN PATENT DOCUMENTS

| CN | 102854205 | 1/2013 |
| JP | 05-288540 | 11/1993 |

(Continued)

OTHER PUBLICATIONS

Japanese Office Action dated Feb. 1, 2017 issued in Application No. 2016-544283.

(Continued)

*Primary Examiner* — Don Wong
(74) *Attorney, Agent, or Firm* — KED & Associates, LLP (57) ABSTRACT

The method of an embodiment includes the steps of: obtaining a first rocking curve with respect to a wafer obtained using an X-ray diffraction device; setting an X-ray incident angle range having a higher intensity than a reference level in the first rocking curve, calculating an inter-plane spacing for the set X-ray incident angle, calculating a strain value of the wafer using the calculated inter-plane spacing, and calculating sampled strain values on the basis of the calculated strain value; modeling a thickness according to the degree of damage of the wafer on the basis of the intensities of X-ray diffraction beams corresponding to the sampled strain values; obtaining a second rocking curve on the basis of the set X-ray incident angle range, the calculated inter-plane spacing, the sampled strain values and the modeled thickness; matching the second rocking curve to the first rocking curve by changing at least one of the X-ray incident angle range, the inter-plane spacing, the sampled strain values and the modeled thickness; and calculating the depth of damage of the wafer on the basis of the matching result.

20 Claims, 11 Drawing Sheets

(58) Field of Classification Search
USPC .................................................... 378/58, 70
See application file for complete search history.

(56) References Cited

FOREIGN PATENT DOCUMENTS

| | | |
|---|---|---|
| JP | 2001-027611 A | 1/2001 |
| JP | 2001-289797 A | 10/2001 |
| JP | 2002-368000 | 12/2002 |
| JP | 2012-122746 | 6/2012 |
| JP | 2013-174524 | 9/2013 |
| KR | 10-2002-0033592 A | 5/2002 |
| KR | 10-0526215 B1 | 11/2005 |
| KR | 10-2007-0065732 A | 6/2007 |
| KR | 10-2009-0046566 A | 5/2009 |

OTHER PUBLICATIONS

Korean Notice of Allowance dated Apr. 21, 2014 issued in Application No. 10-2013-0116346.
International Search Report (with English translation) and Written Opinion dated Sep. 23, 2014 issued in Application No. PCT/KR2014/007480.
Chinese Office Action dated May 31, 2017 issued in Application No. 201480053840.2 (English translation attached).

\* cited by examiner

METHOD OF MEASURING DEPTH OF DAMAGE OF WAFER

CROSS-REFERENCE TO RELATED PATENT APPLICATIONS

This application is a U.S. National Stage Application under 35 U.S.C. §371 of PCT Application No. PCT/KR2014/007480, filed Aug. 12, 2014, which claims priority to Korean Patent Application No. 10-2013-0116346, filed Sep. 30, 2013, whose entire disclosures are hereby incorporated by reference.

TECHNICAL FIELD

Embodiments relate to a method of measuring a depth of mechanical damage to a wafer.

BACKGROUND ART

In general, wafer manufacturing processes may include mechanical surface treatment processes such as ingot grinding, ingot slicing, or lapping.

The surfaces of wafers may be mechanically damaged due to these mechanical surface treatment processes. The mechanical damage to the wafers may be eliminated by grinding or etching the wafers in post-processing such as grinding or etching.

The amount of the wafer to be removed in post-processing may be determined according to the depth of mechanical damage thereto. To this end, measurement for determining the depth of mechanical damage to the wafer must precede the removal.

The method of measuring the depth of mechanical damage to the wafer may include a method using etching or polishing, a method using X-ray diffractometers, a method using Raman spectroscopy, a method using photoluminescence, or the like.

However, since the method using etching or polishing is a destructive method, it may take a long time to polish and heat-treat the wafer. In addition, the method using X-ray diffractometers may merely determine whether or not the wafer is damaged, and may only determine the extent of damage to the wafer in a qualitative manner. In addition, it is impossible for the method using Raman spectroscopy and the method using photoluminescence to measure the depth of damage to the wafer.

DISCLOSURE

Technical Problem

Embodiments provide a method of accurately measuring a depth of mechanical damage to a wafer using a nondestructive method.

Technical Solution

In accordance with an embodiment, a method of measuring a depth of damage to a wafer includes acquiring a first rocking curve for a prepared wafer using an X-ray diffraction apparatus, setting an X-ray incident angle range having a higher intensity than a reference level in the first rocking curve, calculating an interplanar distance for the set X-ray incident angle, calculating strain values of the wafer using the calculated interplanar distance, and extracting sampled strain values based on the calculated strain values, modeling a thickness according to a degree of damage to the wafer, based on an intensity of an X-ray diffraction beam corresponding to each of the sampled strain values, acquiring a second rocking curve, based on the set X-ray incident angle range, the calculated interplanar distance, the sampled strain values, and the modeled thickness, matching the second rocking curve with the first rocking curve by changing at least one of the X-ray incident angle range, the interplanar distance, the sampled strain values, and the modeled thickness, and calculating a depth of damage to the wafer based on the matched result.

The acquiring a first rocking curve may include setting points on the wafer for crystalline evaluation thereof, acquiring X-ray rocking curves at the set points on the wafer, and comparing FWHMs (Full Widths at Half Maximum) of the X-ray rocking curves at the set points on the wafer, so as to acquire the first rocking curve according to the comparison result.

Among the X-ray rocking curves, the X-ray rocking curve having the greatest FWHM may be selected as the first rocking curve.

The intensity of the diffraction beam, at which the first rocking curve is saturated, may be set as the reference level.

Each of the strain values of the wafer may be a ratio between a deduction interplanar distance and a reference interplanar distance, the reference interplanar distance may be an interplanar distance corresponding to the greatest intensity value of the diffraction beam in the first rocking curve, and the deduction interplanar distance may be a difference between the interplanar distance calculated in the calculating an interplanar distance, and the reference interplanar distance.

In the extracting sampled strain values, the sampled strain values may be extracted based on the highest value of the calculated strain values.

The modeling a thickness according to a degree of damage to the wafer may include acquiring the intensity of the X-ray diffraction beam corresponding to each of the sampled strain values, and modeling the thickness according to the degree of damage to the wafer in proportion to the acquired intensity of the X-ray diffraction beam.

The modeling a thickness according to a degree of damage to the wafer may include dividing the wafer into a plurality of sections in a depth direction thereof according the degree of damage thereto, acquiring the intensity of the X-ray diffraction beam corresponding to each of the sampled strain values, and setting a thickness in each of the sections in proportion to the acquired intensity of the X-ray diffraction beam.

In the acquiring a first rocking curve, the wafer may be a semiconductor wafer obtained by slicing a single crystal ingot, or be a wafer obtained by performing at least one of lapping, grinding, and polishing on a surface of the semiconductor wafer.

In the matching the second rocking curve with the first rocking curve, the second rocking curve may be matched with the first rocking curve by adjusting the thickness set in each of the sections.

In the calculating a depth of damage to the wafer, all of the adjusted thicknesses in the sections may be added in order to calculate the depth of damage to the wafer according to the added result.

The points on the wafer for crystalline evaluation thereof may include a center point on the wafer, an edge point on the wafer, and a point located halfway along a radius of the wafer.

The points on the wafer for crystalline evaluation thereof may be located so as to be radially spaced apart from each other.

In accordance with another embodiment, a method of measuring a depth of damage to a wafer includes preparing a wafer, acquiring a first rocking curve for the wafer using an X-ray diffraction apparatus, modeling a thickness according to a degree of damage to the wafer, based on the first rocking curve, acquiring a second rocking curve according to a result of performing a computer simulation, based on the result of the modeling, matching the second rocking curve with the first rocking curve, and calculating a depth of damage to the wafer based on the matched result.

The acquiring a first rocking curve may include acquiring X-ray rocking curves at a center point on the wafer, an edge point on the wafer, and a point located halfway along a radius of the wafer, respectively, and comparing FWHMs (Full Widths at Half Maximum) of the acquired X-ray rocking curves while selecting one having the greatest FWHM from among the acquired X-ray rocking curves as the first rocking curve.

The modeling a thickness according to a degree of damage to the wafer may include setting an intensity of a diffraction beam, at which the first rocking curve is saturated, as a reference level, setting an X-ray incident angle range having a higher intensity than the reference level, calculating an interplanar distance for the set X-ray incident angle using Bragg's law, calculating strain values of the wafer using the calculated interplanar distance, extracting sampled strain values based on the highest value of the calculated strain values, and modeling the thickness according to the degree of damage to the wafer, based on an intensity of an X-ray diffraction beam corresponding to each of the sampled strain values.

Each of the strain values of the wafer may be a ratio between a deduction interplanar distance and a reference interplanar distance, the reference interplanar distance may be an interplanar distance corresponding to the greatest intensity value of the diffraction beam in the first rocking curve, and the deduction interplanar distance may be a difference between the interplanar distance calculated in the calculating an interplanar distance, and the reference interplanar distance.

The modeling a thickness according to a degree of damage to the wafer may include dividing the wafer into a plurality of sections in a depth direction thereof according the degree of damage thereto, acquiring the intensity of the X-ray diffraction beam corresponding to each of the sampled strain values, and setting a thickness in each of the sections in proportion to the acquired intensity of the X-ray diffraction beam.

In the acquiring a second rocking curve, the second rocking curve may be acquired based on the set X-ray incident angle, the interplanar distance calculated for the set X-ray incident angle, the sampled strain values, and the modeled thickness.

In the matching the second rocking curve with the first rocking curve, the second rocking curve may be matched with the first rocking curve by adjusting the thickness set in each of the sections.

Advantageous Effects

Embodiments can accurately measure a depth of mechanical damage to a wafer using a nondestructive method.

BEST MODE

Reference will now be made in detail to the exemplary embodiments of the present disclosure, examples of which are illustrated in the accompanying drawings. It will be understood that when a layer (film), a region, a pattern, or an element is referred to as being "on" or "under" another layer (film), region, pattern, or, element, it can be directly on/under the layer, region, pattern, or, element, and one or more intervening elements may also be present. When an element is referred to as being "on" or "under", "under the element" as well as "on the element" can be included based on the element.

In the drawings, the size of each layer is exaggerated, omitted, or schematically illustrated for convenience of description and clarity. Also, the size of each constituent element does not entirely reflect the actual size thereof. In addition, the same reference numbers will be used throughout the drawings to refer to the same or like parts. Hereinafter, a method of measuring mechanical damage to a wafer according to embodiments will be described with reference to the accompanying drawings.

Figure 1:
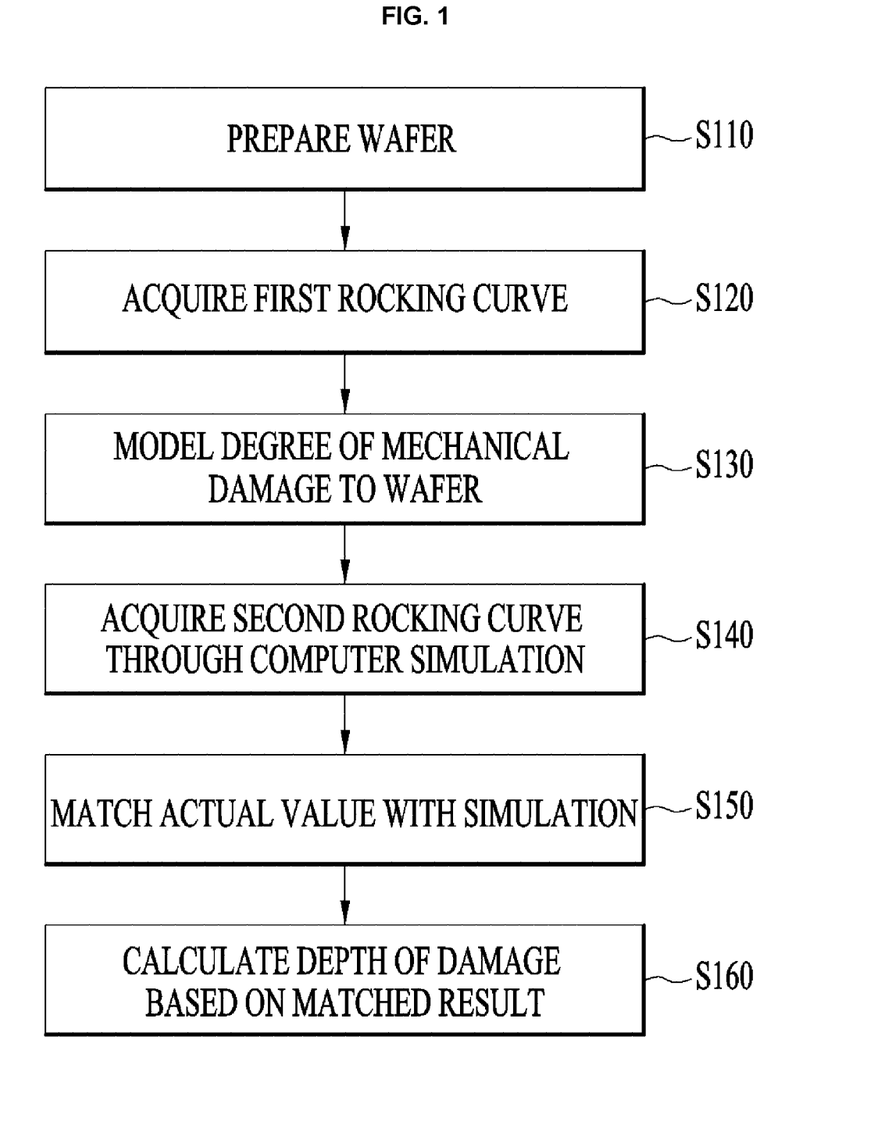
FIG. 1 is a flowchart illustrating a method of detecting mechanical damage to a wafer according to an embodiment.

FIG. 1 is a flowchart illustrating a method of detecting mechanical damage to a wafer according to an embodiment.

Referring to FIG. 1, the method first prepares a wafer for detecting mechanical damage thereto (S110).

In this case, the prepared wafer may be a semiconductor wafer which is obtained by growing a single crystal ingot, and performing ingot grinding, cropping, and slicing processes on the grown single crystal ingot. For example, the semiconductor wafer may include single crystal wafers such as sapphire wafers.

In addition, the prepared wafer may be a wafer obtained by performing at least one of lapping, grinding, etching, and polishing processes on the surface of the semiconductor wafer.

Next, the method acquires a first rocking curve for the prepared wafer using an X-ray diffraction apparatus (S120).

For example, the first rocking curve may be acquired based on the result of crystalline evaluation performed on the prepared wafer.

For example, the crystalline evaluation is performed on predetermined points on the prepared wafer at different positions thereof, and a point on the wafer having the lowest crystallinity may be selected based on the result of the evaluation. The X-ray rocking curve at the selected point on the wafer having the lowest crystallinity may be selected as the first rocking curve.

Figure 2:
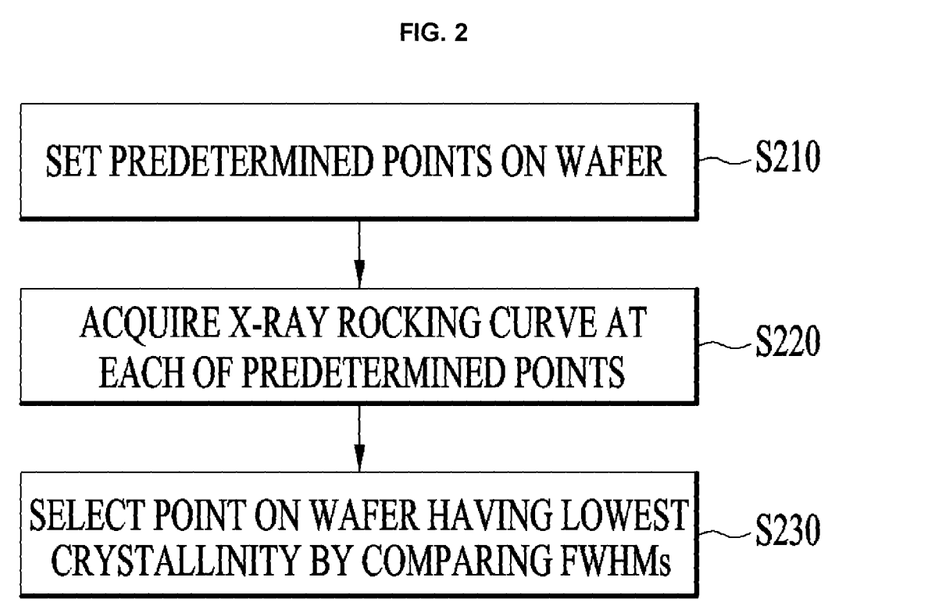
FIG. 2 is a flowchart illustrating an example of the method for crystalline evaluation of the wafer.

FIG. 2 is a flowchart illustrating an example of the method for crystalline evaluation of the wafer.

Referring to FIG. 2, the method first sets points on the wafer for crystalline evaluation thereof (S210).

For example, the predetermined points on the wafer for crystalline evaluation thereof may be a center point, an edge point, and a point located halfway along a radius of the wafer, but the number and positions of predetermined points are not limited thereto. Alternatively, the predetermined points may be radially spaced apart from each other.

Next, the method acquires an X-ray rocking curve at each of the predetermined points using the X-ray diffraction apparatus (S220).

When any crystal is irradiated with an X-ray, the angle of diffraction of the X-ray on the specific surface of the crystal may be determined by Bragg's law. In this case, when the crystal is absolutely perfect, the intensity of the X-ray diffraction beam may be expressed as a single line.

On the other hand, when the crystal has a defect, e.g. a defect in the shape of a point, line, surface, or volume, therein, the intensity of the X-ray diffraction beam may be expressed as a Gaussian distribution curve, rather than a single line. The Gaussian distribution curve may be referred to as the X-ray rocking curve.

Figure 3:
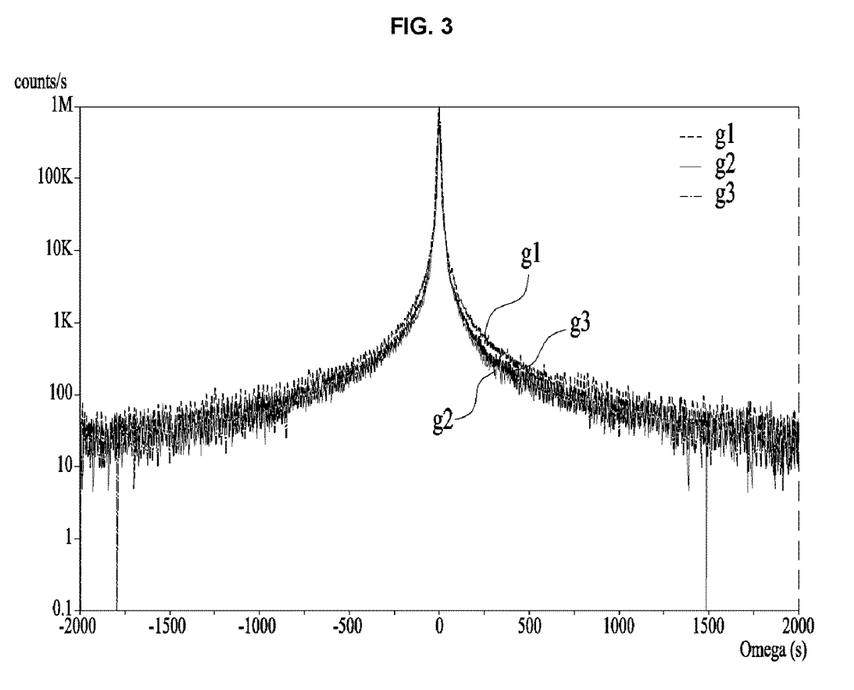
FIG. 3 is a graph illustrating X-ray rocking curves at predetermined points on the wafer.

FIG. 3 is a graph illustrating X-ray rocking curves at the predetermined points on the wafer.

The x-axis refers to an X-ray incident angle, and the y-axis refers to the intensity of an X-ray diffraction beam. The g1 may refer to an X-ray rocking curve at the center point on the wafer (hereinafter, referred to as a "first point"), the g2 may refer to an X-ray rocking curve at the point located halfway along the radius of the wafer (hereinafter, referred to as a "second point"), and the g3 may refer to an X-ray rocking curve at the edge point on the wafer (hereinafter, referred to as a "third point").

Referring to FIG. 3, it may be seen that the X-ray rocking curves g1, g2, and g3 at the first to third points are Gaussian curves, and a crystal defect is present in each of the first to third points.

Next, the method selects a point on the wafer having the lowest crystallinity or a point on the wafer having the poorest crystallinity by comparing the FWHMs (Full Widths at Half Maximum) of the X-ray rocking curves g1, g2, and g3 at the predetermined points (S230). Here, each FWHM is a width between values which are half of a maximum intensity value in the associated rocking curve.

The good crystallinity may mean that a defect is rarely present in the wafer. The significant mechanical damage to the surface of the wafer may mean that the wafer has many defects on the surface thereof due to physical force. As the FWHM value of the rocking curve is increased, the defect may be increased in the wafer.

The low crystallinity of the wafer on the predetermined points thereon may be proportional to the FWHMs at the predetermined points on the wafer.

Referring to the rocking curves g1, g2, and g3 at the predetermined points illustrated in FIG. 3, it may be seen that the rocking curve g1 has the greatest FWHM at the first point on the wafer. Accordingly, it may be determined that the crystallinity of the wafer is lowest at the first point on the wafer, and the first point on the wafer may be selected as the lowest point.

Next, the method models a thickness according to the degree of damage to the wafer in the depth direction of the wafer, based on the first rocking curve (S130).

Figure 4:
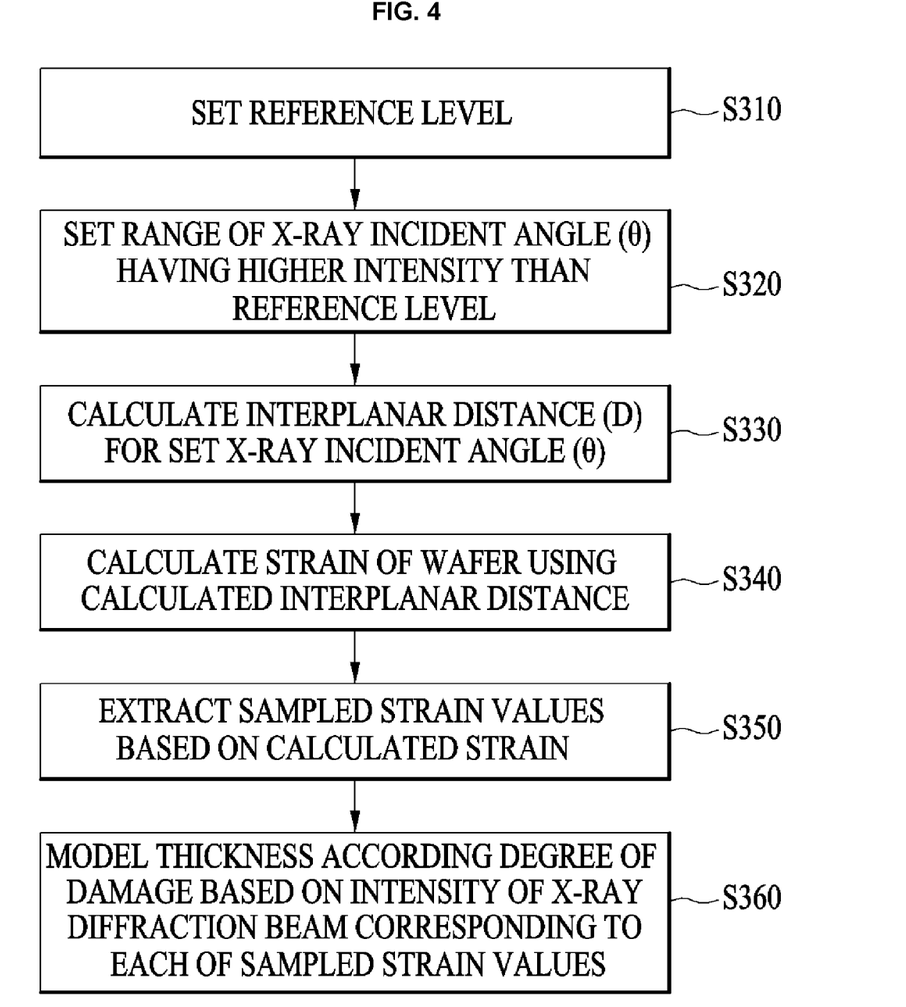
FIG. 4 is a flowchart illustrating an example of the modeling step illustrated in FIG. 1.
Figure 5:
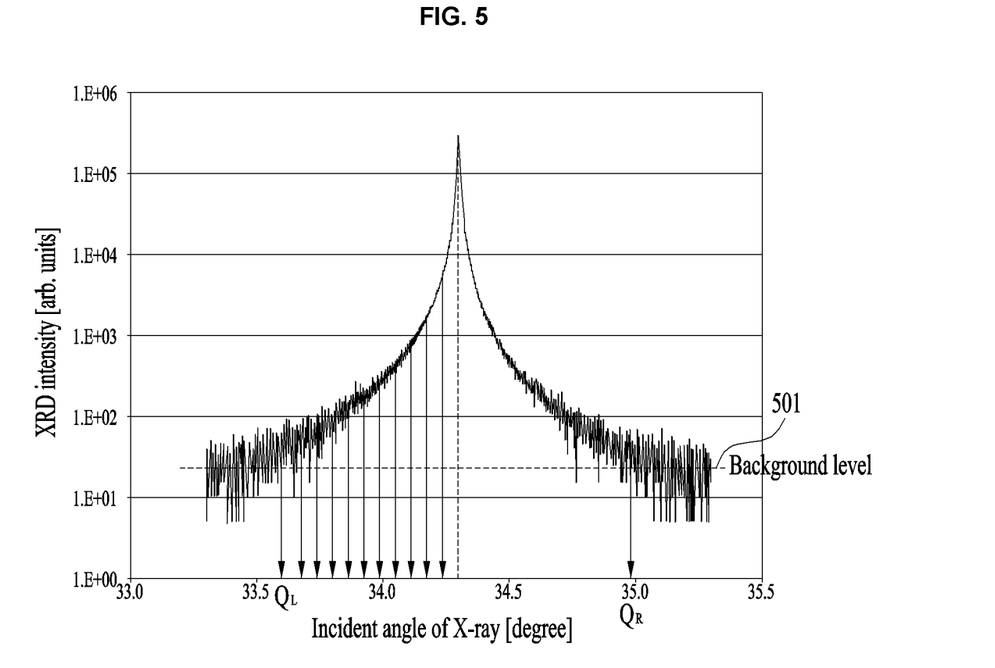
FIG. 5 is a graph illustrating an example of a first rocking curve for explaining the modeling step illustrated in FIG. 4.

FIG. 4 is a flowchart illustrating an example of the modeling step (S130) illustrated in FIG. 1. FIG. 5 is a graph illustrating an example of the first rocking curve for explaining the modeling step (S130) illustrated in FIG. 4.

Referring to FIGS. 4 and 5, the method sets a reference level (or background level) 501 for the first rocking curve (S310). The first rocking curve illustrated in FIG. 5 may be a rocking curve at the point on the wafer having the lowest crystallinity, which is selected in step S120, but the present embodiment is not limited thereto. For example, the first rocking curve may be one of the rocking curves at the predetermined points in step S210.

When the X-ray incident angle, which is the x-axis range of the first rocking curve, is sufficiently large during XRD measurement, the intensity of the X-ray diffraction beam, at which the first rocking curve is saturated, may be set as a reference level or a background level. This is because the intensity or base level of the diffraction beam in the first rocking curve during XRD measurement may be changed according to power, slit size, X-ray tube lifetime, and sample states which are XRD measurement conditions.

Here, the reference level may be assumed as noise in the measurement state. When the rocking curve is saturated, it is necessary to set the above reference level. If Bragg's law is not satisfied, the intensity of the diffraction beam should be theoretically zero (0) at a point except for the point at which the intensity of the diffraction beam peaks. However, the reference level may be measured at the above point.

Next, the method sets a range ($\theta L \sim \theta R$) of an X-ray incident angle ($\theta$) having a higher intensity than the reference level 501 (S320) in the X-ray rocking curve. In this case, the set range ($\theta L \sim \theta R$) of an X-ray incident angle ($\theta$) may be determined according to the types of the wafer, or the surface or crystal state of the wafer.

For example, in a silicon wafer, the processed surface of the wafer may be a (100) surface. Since the diffraction of the silicon does not occur on the (100) surface due to an X-ray structure factor, the rocking curve may be measured on a (400) surface, which is parallel with the (100) surface and on which diffraction occurs, by an X-ray diffraction method. Accordingly, the crystal surface of the wafer, on which diffraction does not occur, may be set as a reference surface.

For example, the intensity of the X-ray may be measured by changing the incident angle of the X-ray incident on the (400) surface in the state in which the angle of an X-ray detector is fixed. The range ($\theta L \sim \theta R$) of an X-ray incident angle ($\theta$) having a higher intensity than the reference level 501 may be a range of substantially about 33.6° to 35.0°.

However, when the processed surface of the wafer is changed, the range of an X-ray incident angle ($\theta$) may be changed. For example, since the crystal surface of a (111) wafer or a (110) wafer, on which X-ray diffraction is measured, is changed in itself, the range of an X-ray incident angle ($\theta$) in the (111) or (110) wafer may differ from that in the silicon wafer. In addition, the range of an X-ray incident angle ($\theta$) in a sapphire wafer may differ from that in the silicon wafer.

Here, the (100) wafer may refer to a wafer, the processed surface (front side or back side) of which has a (100) index. Each of the (111) and (110) wafers may also refer to a wafer, the processed surface of which is a (111) or (110) crystal surface from among the crystal surfaces of the silicon. The (100) surface may refer to the crystal surface of the silicon, the Miller index of which is (100). Here, the processing may refer to ingot slicing, and may include lapping, grinding, polishing, and etching, besides the slicing.

In general, the silicon wafer is not sliced on the reference surface, e.g. on the (100) surface, but may be sliced in a direction inclined by an off-angle from the (100) surface. Here, the off-angle may be determined according to the request of a user.

Hereinafter, the wafer, the processed surface of which coincides with the reference surface, is referred to as a first wafer, and the wafer, the processed surface of which is inclined by an off-angle from the reference surface, is referred to as a second wafer.

The angle indicative of the peak value of the rocking curve on the first wafer may coincide with the angle indicative of the peak value of the rocking curve on the reference surface (hereinafter, referred to as a "first angle").

Since an interplanar distance and an X-ray wavelength are determined on the reference surface, e.g. on the (400) surface of the silicon, the angle (e.g. 34.566°) indicative of the peak value may be obtained by Bragg's law.

On the other hand, the angle indicative of the peak value of the rocking curve on the second wafer (hereinafter, referred to as a "second angle") may not coincide with the angle indicative of the peak value of the rocking curve on the reference surface, and the difference between angles may be generated.

Accordingly, it is necessary to correct the rocking curve for the second wafer as follows. In the second wafer, the range of an X-ray incident angle ($\theta$) having a higher intensity than the reference level 501 may be set using the corrected rocking curve, and the following procedures may be performed based on the corrected rocking curve.

That is, it is possible to correct the angle of the rocking curve for the second wafer by the difference between the first and second angles. For example, the rocking curve for the second wafer may be moved in parallel in the x-axis direction by the difference between the first and second angles.

Next, the method calculates an interplanar distance (d) for the set range ($\theta L \sim \theta R$) of an X-ray incident angle ($\theta$), using Bragg's law of $\lambda = 2d \sin \theta$ (S330).

Here, the interplanar distance (d) may be a distance between the reference surfaces of the wafer.

For example, the interplanar distance (d) on the silicon wafer may refer to a distance between (400) surfaces. That is, the interplanar distance (d) may refer to a distance between the (400) surfaces which are damaged and deformed by mechanical processing.

Next, the method calculates strain values of the wafer in the range ($\theta L \sim \theta R$) of an X-ray incident angle ($\theta$), using the calculated interplanar distance (d) (S340). The strain may mean a ratio of the interplanar distance (d) changed by mechanical factors to a reference interplanar distance (d0).

For example, each strain value of the wafer may be a ratio (d1/d0) between a deduction interplanar distance (d1) and a reference interplanar distance (d0).

The reference interplanar distance (d0) may be a distance between the reference surfaces of the wafer.

The reference interplanar distance (d0) may be an interplanar distance corresponding to the greatest intensity value of the diffraction beam in the first rocking curve. For example, the reference interplanar distance (d0) may be an interplanar distance where the intensity of the diffraction beam is the greatest in the first rocking curve.

For example, the reference interplanar distance (d0) for the (400) surface of the silicon may be 1.3577 Angstroms (Å).

The deduction interplanar distance (d1) may be a difference between the interplanar distance (d) calculated in step S330 and the reference interplanar distance (d0).

Next, the method samples the strain values calculated corresponding to the range ($\theta L \sim \theta R$) of an X-ray incident angle ($\theta$), and extracts the sampled strain values (S350).

For example, the sampled strain values may be extracted based on the highest value of the calculated strain values. The sampled strain values may be extracted by reducing the highest value of the calculated strain values by a certain value.

For example, the difference between the sampled strain values may be 50 ppm to 150 ppm, but the embodiment is not limited thereto. The ppm is an abbreviation of parts-per million, and refers to $10^{-6}$.

For example, when the highest value of the calculated strain values is assumed to be 1000 ppm, samples (e.g. 1000 ppm, 900 ppm, 800 ppm, 700 ppm, etc.) may be extracted by reducing the strain values by 100 ppm.

Next, the method may model a thickness according to the degree of mechanical damage to the wafer, based on the intensity of the X-ray diffraction beam corresponding to each of the extracted and sampled strain values (S360).

The interplanar distance (d) may be calculated from the extracted strain values, the X-ray incident angle ($\theta$) corresponding to the calculated interplanar distance (d) may be calculated using Bragg's law, and the intensity of the X-ray diffraction beam corresponding to the calculated X-ray incident angle ($\theta$) may be obtained using the first rocking curve. It is possible to model a thickness according to the degree of mechanical damage to the wafer in proportion to the obtained intensity of the X-ray diffraction beam.

For example, the wafer may be divided into a plurality of sections in the depth direction of the wafer according to the degree of mechanical damage to the wafer. The thickness in each of the sections may be set based on the intensity of the X-ray diffraction beam corresponding to the each of the sampled strain values.

For example, the thickness in each section may be set in proportion to the intensity of the X-ray diffraction beam corresponding to the each of the sampled strain values. Since the intensity of the beam is changed in itself according to measurement conditions, the thickness in each section may be substantially set based on the intensity of the X-ray diffraction beam.

Figure 6:
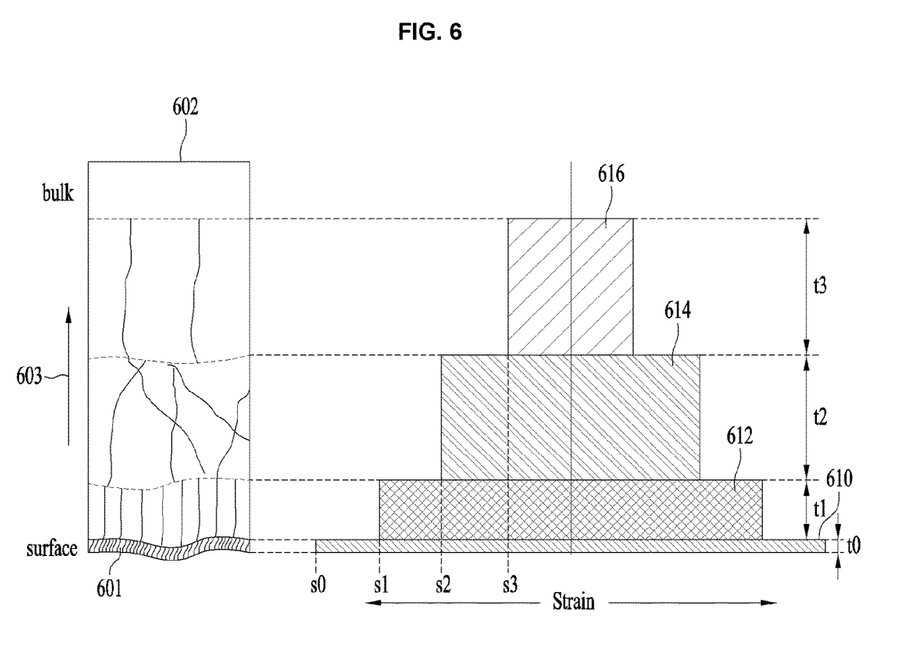
FIG. 6 is a diagram for explaining modeling of the degree of mechanical damage to the wafer illustrated in FIG. 4.

FIG. 6 is a diagram for explaining modeling of the degree of mechanical damage to the wafer illustrated in FIG. 4.

Referring to FIG. 6, the degree of mechanical damage to the wafer may be severe on the surface of the wafer, and the degree of mechanical damage may be reduced in the depth direction 603 of the wafer. In addition, no mechanical damage may occur in a predetermined depth or more.

Here, the surface 601 of the wafer may be a wafer surface on which an X-ray is incident, a bulk 602 may be located inside the wafer. The depth direction 603 of the wafer may be a direction that is directed to the bulk 602 from the surface 601 of the wafer.

The wafer may be divided into a plurality of sections (e.g. 612, 614, and 616) in the depth direction 603 of the wafer according to the degree of mechanical damage thereto. The first section (e.g. 612) adjacent to the wafer surface 601 may have the highest strain value, and the degree of mechanical damage may be the highest in the first section. In addition, the third section (e.g. 606) adjacent to the bulk 602 may have the lowest strain value, and the degree of mechanical damage may be the lowest in the third section.

The thicknesses (t1, t2, and t3) in the respective sections (e.g. 612, 614, and 616) may be set based on the intensities of X-ray diffraction beams corresponding to the respective sampled strain values (S1, S2, and S3).

The thicknesses (t1, t2, and t3) in the respective sections (e.g. 612, 614, and 616) may be set as follows.

For example, when the highest value of the calculated strains is assumed to be 1000 ppm, it is possible to set the sections (e.g. 612, 614, and 616) by reducing the strain values by 100 ppm.

The degree of damage to the wafer is reduced toward the bulk from the wafer surface. Therefore, even when the strain is divided at a regular interval of 100 ppm, the thickness in each section may be significantly increased as the strain value is small.

As illustrated in FIG. 6, when the strain is divided into the sections (S0, S1, S2, and S3), the thicknesses for each same strain may be increased (t0<t1<t2<t3).

It is possible to sample strain values and determine sections 610, 612, 614, and 616 corresponding to the samples values (S0, S1, S2, and S3). In this case, as the sampled strain value is increased, the section corresponding thereto may be disposed on the bottom (e.g. S0—610).

The thicknesses (t0, t1, t2, and t3) in the respective sections 610, 612, 614, and 616 may be set in proportion to the intensities of diffraction beams corresponding to the respective sampled strain values (S0, S1, S2, and S3).

As seen in the first rocking curve of FIG. 5, when the strain is divided at a regular interval from the strain value at the point indicative of a higher intensity than the reference level 501, it may be seen that the intensity of the X-ray diffraction beam may be rapidly increased according to a reduction in strain.

Next, the method performs a computer simulation based on the result of modeling the degree of mechanical damage to the wafer, and acquires the second rocking curve according to the simulated result (S140).

The computer simulation may be performed based on the result of the modeling and the data of the measurement conditions in step S130, and the second rocking curve may be acquired according the simulated result.

Here, the result of the modeling in step S130 may mean the strains (e.g. S0, S1, S2, and S3) and the thicknesses (t0, t1, t2, and t3). In addition, the measurement conditions may include the peak intensity of the first rocking curve, the intensity of the reference level, the optical condition of the X-ray diffraction apparatus, and the measurement spacing of the x-axis, and the sect X-ray incident angle range of the first rocking curve.

FIGS. 7A to 7D are graphs illustrating the actual value of the first rocking curve and the process of matching the second rocking curve therewith based on the simulated result, according to the embodiment.

Figure 7A:
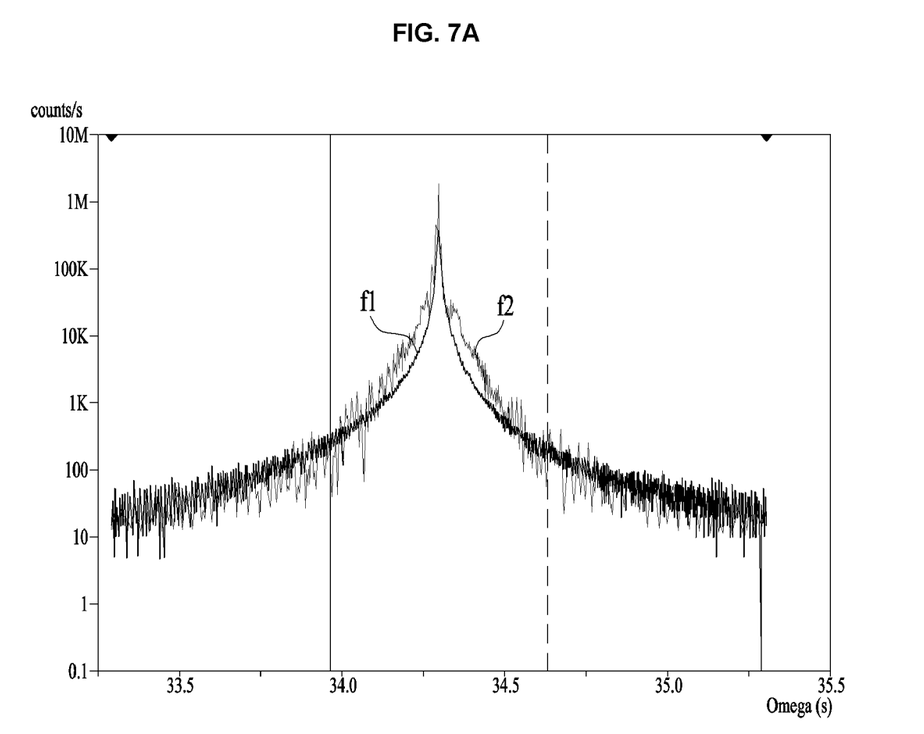
FIGS. 7A to 7D are graphs illustrating the actual value of the first rocking curve and the process of matching a second rocking curve therewith based on the simulated result, according to the embodiment.

The f1 refers to an actual value of the first rocking curve acquired in step S220.

The f2 refers to a second rocking curve according to the result of the computer simulation performed in step S140.

Figure 7B:
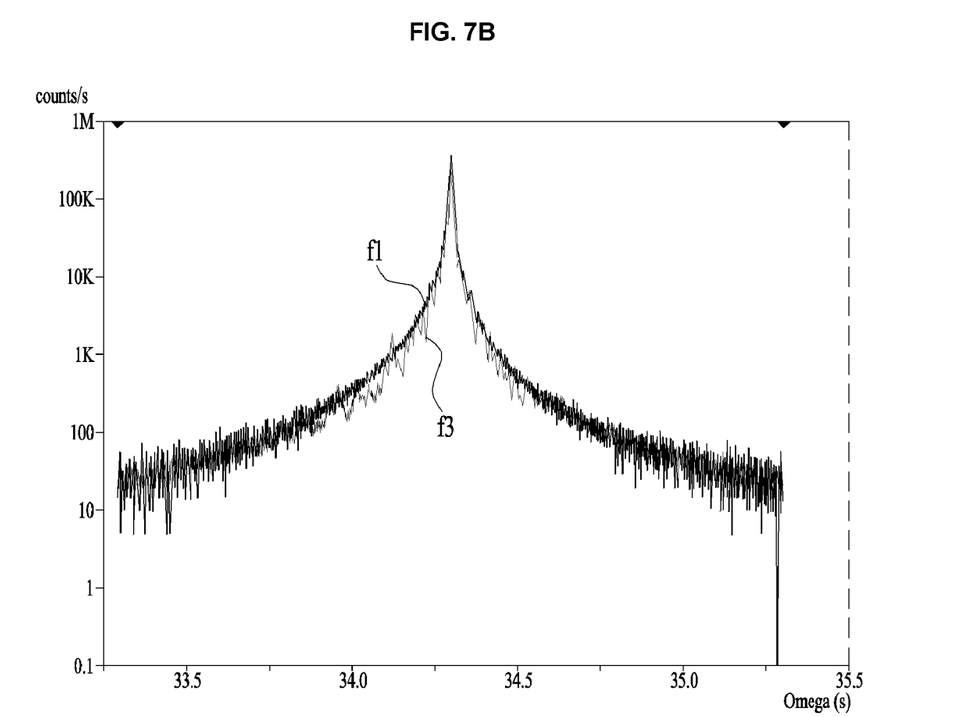
Figure 7C:
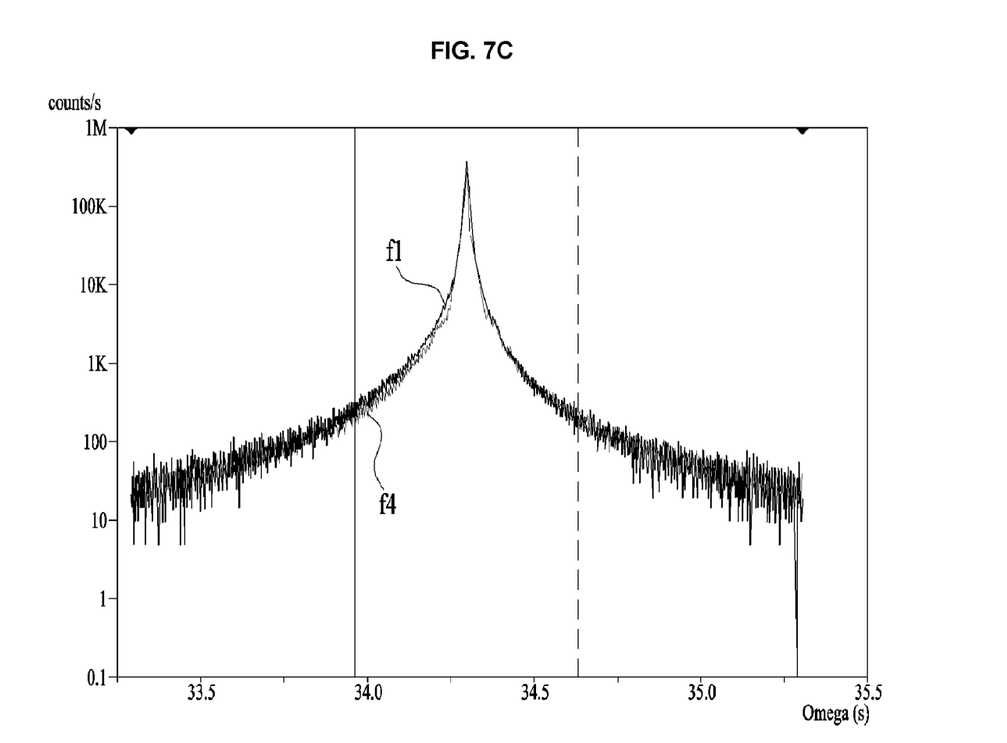
Figure 7D:
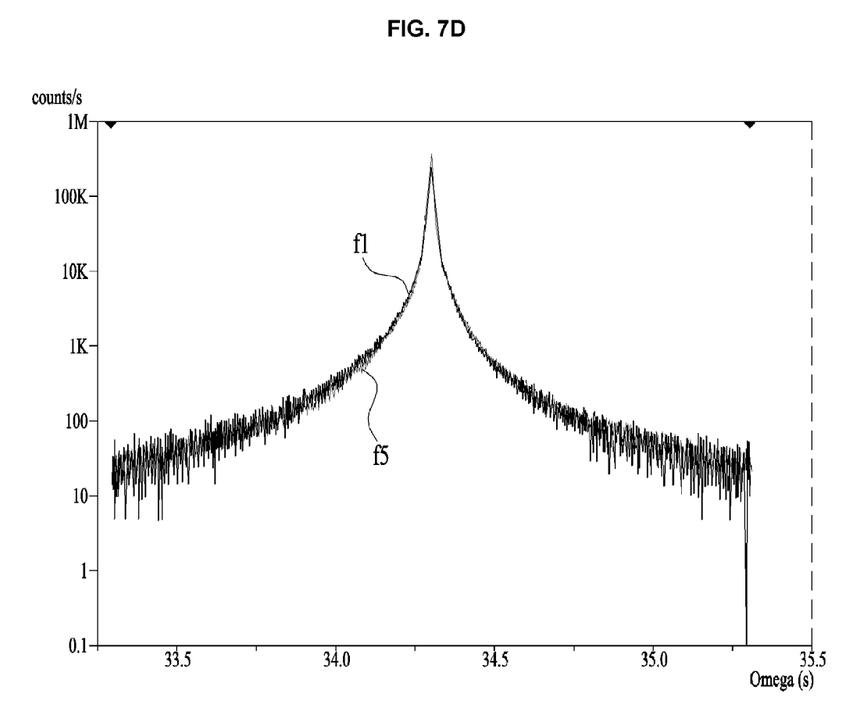

The f3 refers to a second rocking curve according to the result of the computer simulation by first matching. The f4 refers to a second rocking curve according to the result of the computer simulation by second matching. The f5 refers to a second rocking curve according to the result of the computer simulation by third matching.

In order to calculate the second rocking curve illustrated in FIG. 7a using a computer simulation program for calculating X-ray rocking curves, the computer simulation may be performed based on the range of an X-ray incident angle (θ) set in step S320, the interplanar distance (d) calculated in step S330, the strain values extracted and sampled in step S350, and the thickness in each section molded and set in step S360.

Next, the method matches the actual value of the first rocking curve acquired in step S220 with the second rocking curve acquired in step S140 (S150).

For example, the second rocking curve may coincide with the actual value of the first rocking curve by changing at least one of the position of the peak intensity of the second rocking curve, the range of an X-ray incident angle (θ), the interplanar distance (d), the sampled strain values, and the thicknesses in the respective sections.

For example, the second rocking curve (e.g. f2 in FIG. 7) may match or coincide with the actual value (e.g. f1 in FIG. 7) of the first rocking curve by adjusting the sampled strain values or the thicknesses (e.g. t1, t2, and t3) in the respective sections (e.g. 612, 614, and 616). As illustrated in FIGS. 7B to 7D, the matching process may be repeatedly performed in many times.

Next, the method calculates the depth of damage to the wafer based on the matched result (S160).

It may be analyzed that the coincidence between the simulated result in step S150 and the actual value in step S220 means that the thickness set for each of the sampled strain values input according to the simulated result coincides with the actual depth of damage to the wafer.

Accordingly, the depth of damage to the wafer may be calculated by adding all of thicknesses adjusted corresponding to the respective sampled strain values input according to the result of the matching simulation in step S150.

The embodiment can determine the depth of mechanical damage to the wafer using a nondestructive method, and can easily determine the depth of mechanical damage to a sapphire wafer which is difficult to be etched.

It may be seen that the depth of damage to the wafer measured according to the embodiment is larger than the depth of damage to the same wafer measured according to the method using etching and polishing. This means that the embodiment may accurately measure the depth of small damage compared to the method using etching and polishing. That is, the embodiment may more accurately measure the depth of mechanical damage to the wafer, compared to the method using etching and polishing.

Figure 8:
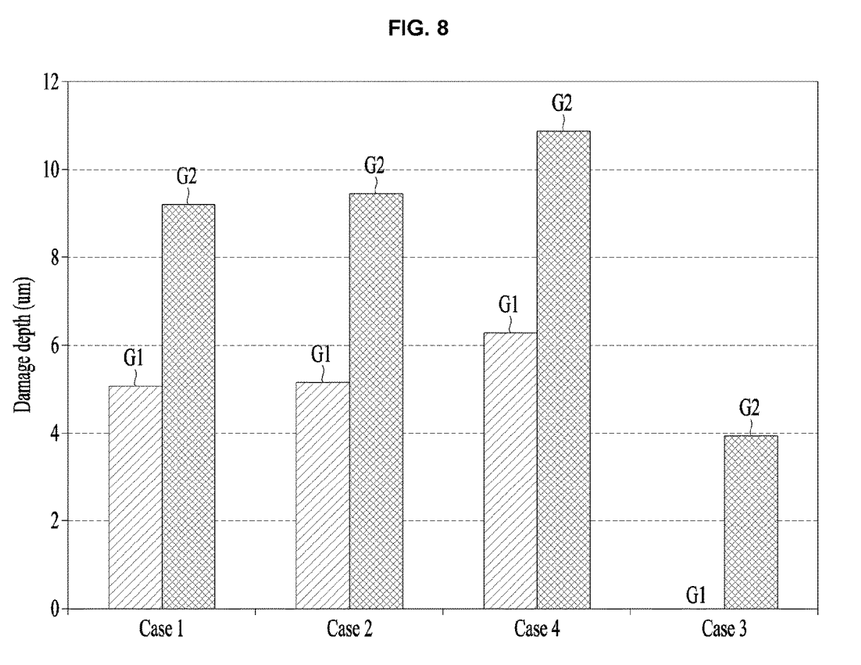
FIG. 8 is a graph illustrating a depth of damage measured according to a method using etching and polishing and a method of the embodiment.

FIG. 8 is a graph illustrating the depth of damage measured according to a method using etching and polishing G1 and a method of the embodiment G2. Case 1 illustrates a result of measuring the depth of damage to the wafer after a slicing process is completed. Case 2 illustrates a result of measuring the depth of damage to the wafer after a lapping process is completed. Case 3 illustrates a result of measuring the depth of damage to the wafer before an OISF heat treatment process is performed after a grinding process is completed. Case 4 illustrates a result of measuring the depth of damage to the wafer after a grinding process and an OISF heat treatment process are completed.

Referring to FIG. 8, it may be seen that the depth of damage in the G2 is observed to be larger by 4 μm to 4.5 μm, compared to the depth of damage in the G1. This is because, when the wafer is etched for 30 seconds and is then observed using a microscope for visualization in the G1, a damage layer may be observed through the etching in the vicinity of the surface of the wafer having large damage, but the damage layer may not be observed through the etching in the region of the bulk of the wafer having small damage.

Since the G1 slices, polishes, and etches the wafer, there are problems in that it takes a long time to measure the depth of damage thereto and the wafer is analyzed in a destructive manner. In addition, the depth of damage is not measured in the Case 3 in the G1. For this reason, since the depth of damage must be measured after the OISF heat treatment, it takes a long time to measure the depth of damage.

On the other hand, the embodiment has an advantage of a nondestructive manner in measuring the depth of damage. In addition, it takes a long time for the embodiment to initially perform a modeling and match an actual value through a computer simulation using the performed modeling. However, after a prototype model is established, the depth of damage to the wafer can be evaluated for a short time by slightly changing each sample based on the prototype model.

Particular features, structures, or characteristics described in connection with the embodiment are included in at least one embodiment of the present disclosure and not necessarily in all embodiments. Furthermore, the particular features, structures, or characteristics of any specific embodiment of the present disclosure may be combined in any suitable manner with one or more other embodiments or may be changed by those skilled in the art to which the embodiments pertain. Therefore, it is to be understood that contents associated with such combination or change fall within the spirit and scope of the present disclosure.

INDUSTRIAL APPLICABILITY

Embodiments are applicable to wafer manufacturing processes.

The invention claimed is:

1. A method of measuring a depth of damage to a wafer, comprising:
    acquiring a first rocking curve for a prepared wafer using an X-ray diffraction apparatus;
    setting an X-ray incident angle range having a higher intensity than a reference level in the first rocking curve, calculating an interplanar distance for the set X-ray incident angle, calculating strain values of the wafer using the calculated interplanar distance, and extracting sampled strain values based on the calculated strain values;
    modeling a thickness according to a degree of damage to the wafer, based on an intensity of an X-ray diffraction beam corresponding to each of the sampled strain values;
    acquiring a second rocking curve, based on the set X-ray incident angle range, the calculated interplanar distance, the sampled strain values, and the modeled thickness;
    matching the second rocking curve with the first rocking curve by changing at least one of the X-ray incident angle range, the interplanar distance, the sampled strain values, and the modeled thickness; and
    calculating a depth of damage to the wafer based on the matched result.

2. The method according to claim 1, wherein the acquiring a first rocking curve comprises:
    setting points on the wafer for crystalline evaluation thereof;
    acquiring X-ray rocking curves at the set points on the wafer; and
    comparing FWHMs (Full Widths at Half Maximum) of the X-ray rocking curves at the set points on the wafer, so as to acquire the first rocking curve according to the comparison result.

3. The method according to claim 2, wherein, among the X-ray rocking curves, the X-ray rocking curve having the greatest FWHM is selected as the first rocking curve.

4. The method according to claim 1, wherein the intensity of the diffraction beam, at which the first rocking curve is saturated, is set as the reference level.

5. The method according to claim 1, wherein each of the strain values of the wafer is a ratio between a deduction interplanar distance and a reference interplanar distance, the reference interplanar distance is an interplanar distance corresponding to the greatest intensity value of the diffraction beam in the first rocking curve, and the deduction interplanar distance is a difference between the interplanar distance calculated in the calculating an interplanar distance, and the reference interplanar distance.

6. The method according to claim 1, wherein, in the extracting sampled strain values, the sampled strain values are extracted based on the highest value of the calculated strain values.

7. The method according to claim 1, wherein the modeling a thickness according to a degree of damage to the wafer comprises:
    acquiring the intensity of the X-ray diffraction beam corresponding to each of the sampled strain values; and
    modeling the thickness according to the degree of damage to the wafer in proportion to the acquired intensity of the X-ray diffraction beam.

8. The method according to claim 1, wherein the modeling a thickness according to a degree of damage to the wafer comprises:
    dividing the wafer into a plurality of sections in a depth direction thereof according the degree of damage thereto;
    acquiring the intensity of the X-ray diffraction beam corresponding to each of the sampled strain values; and
    setting a thickness in each of the sections in proportion to the acquired intensity of the X-ray diffraction beam.

9. The method according to claim 1, wherein, in the acquiring a first rocking curve, the wafer is a semiconductor wafer obtained by slicing a single crystal ingot, or is a wafer obtained by performing at least one of lapping, grinding, and polishing on a surface of the semiconductor wafer.

10. The method according to claim 8, wherein, in the matching the second rocking curve with the first rocking curve, the second rocking curve is matched with the first rocking curve by adjusting the thickness set in each of the sections.

11. The method according to claim 10, wherein, in the calculating a depth of damage to the wafer, all of the adjusted thicknesses in the sections are added in order to calculate the depth of damage to the wafer according to the added result.

12. The method according to claim 2, wherein the points on the wafer for crystalline evaluation thereof comprise a center point on the wafer, an edge point on the wafer, and a point located halfway along a radius of the wafer.

13. The method according to claim 2, wherein the points on the wafer for crystalline evaluation thereof are located so as to be radially spaced apart from each other.

14. A method of measuring a depth of damage to a wafer, comprising:
    preparing a wafer;
    acquiring a first rocking curve for the wafer using an X-ray diffraction apparatus;
    modeling a thickness according to a degree of damage to the wafer, based on the first rocking curve;
    acquiring a second rocking curve according to a result of performing a computer simulation, based on the result of the modeling;

matching the second rocking curve with the first rocking curve; and calculating a depth of damage to the wafer based on the matched result.

15. The method according to claim 14, wherein the acquiring a first rocking curve comprises:

acquiring X-ray rocking curves at a center point on the wafer, an edge point on the wafer, and a point located halfway along a radius of the wafer, respectively; and comparing FWHMs (Full Widths at Half Maximum) of the acquired X-ray rocking curves while selecting one having the greatest FWHM from among the acquired X-ray rocking curves as the first rocking curve.

16. The method according to claim 14, wherein the modeling a thickness according to a degree of damage to the wafer comprises:

setting an intensity of a diffraction beam, at which the first rocking curve is saturated, as a reference level;

setting an X-ray incident angle range having a higher intensity than the reference level;

calculating an interplanar distance for the set X-ray incident angle using Bragg's law;

calculating strain values of the wafer using the calculated interplanar distance;

extracting sampled strain values based on the highest value of the calculated strain values; and modeling the thickness according to the degree of damage to the wafer, based on an intensity of an X-ray diffraction beam corresponding to each of the sampled strain values.

17. The method according to claim 16, wherein each of the strain values of the wafer is a ratio between a deduction interplanar distance and a reference interplanar distance, the reference interplanar distance is an interplanar distance corresponding to the greatest intensity value of the diffraction beam in the first rocking curve, and the deduction interplanar distance is a difference between the interplanar distance calculated in the calculating an interplanar distance, and the reference interplanar distance.

18. The method according to claim 16, wherein the modeling a thickness according to a degree of damage to the wafer comprises:

dividing the wafer into a plurality of sections in a depth direction thereof according the degree of damage thereto;

acquiring the intensity of the X-ray diffraction beam corresponding to each of the sampled strain values; and setting a thickness in each of the sections in proportion to the acquired intensity of the X-ray diffraction beam.

19. The method according to claim 16, wherein, in the acquiring a second rocking curve, the second rocking curve is acquired based on the set X-ray incident angle, the interplanar distance calculated for the set X-ray incident angle, the sampled strain values, and the modeled thickness.

20. The method according to claim 18, wherein, in the matching the second rocking curve with the first rocking curve, the second rocking curve is matched with the first rocking curve by adjusting the thickness set in each of the sections.

* * * * *